United States Patent
Kåhre

[11] Patent Number: 5,617,201
[45] Date of Patent: Apr. 1, 1997

[54] METHOD FOR REFRACTOMETER MEASURING USING MATHEMATICAL MODELLING

[75] Inventor: Jan Kåhre, Helsinki, Finland

[73] Assignee: Janesko Oy, Finland

[21] Appl. No.: 299,752

[22] Filed: Sep. 1, 1994

[30] Foreign Application Priority Data

Sep. 1, 1993 [FI] Finland ................................. 933830

[51] Int. Cl.$^6$ ............................................ G01N 21/41
[52] U.S. Cl. ................................. 356/135; 356/136
[58] Field of Search ............................ 356/135–136, 356/137, 128

[56] References Cited

U.S. PATENT DOCUMENTS 4,640,616  2/1987  Michalik ................................. 356/136

FOREIGN PATENT DOCUMENTS

| | | | |
|---|---|---|---|
| 52-040187 | 3/1977 | Japan | 356/136 |
| 61-011636 | 1/1986 | Japan | 356/136 |
| 61-011637 | 1/1986 | Japan | 356/136 |
| 63-275936 | 11/1988 | Japan | 356/128 |
| 01197633 | 8/1989 | Japan . | |

*Primary Examiner*—Georgia Y. Epps
*Assistant Examiner*—Jason D. Eisenberg
*Attorney, Agent, or Firm*—Fitch, Even, Tabin & Flannery

[57] ABSTRACT

A method for refractometer measuring, in which a beam of rays emitted from a light source is transmitted to the interface between the optical window of a refractometer and the liquid to be measured, whereby part of the beam of rays is reflected back from the liquid and part is absorbed into the liquid and an image is produced in which the position of the boundary between a light and dark area depends on the critical angle of total reflection, the critical angle being a function of concentration of liquid, and in which the boundary between the light and dark area of the image is determined by light detectors arranged in a line. For good resolution, to the measuring data obtained from the light detectors is applied a mathematical model corresponding with the information provided by the measuring data and the position of the boundary is determined by means of this model.

5 Claims, 1 Drawing Sheet

METHOD FOR REFRACTOMETER MEASURING USING MATHEMATICAL MODELLING

BACKGROUND OF THE INVENTION

The invention concerns a method for refractometer measuring, in which a beam of rays emitted from a light source is transmitted to the interface between the optical window of a refractometer and the liquid to be measured, whereby part of the beam of rays is reflected back from the liquid and part is absorbed into the liquid and an image is produced in which the position of the boundary between a light and dark area depends on the critical angle of total reflection, the critical angle being a function of concentration of liquid, and in which the boundary between the light and dark area of the image is determined by light detectors arranged in a line.

The principle of the refractometer has been known for over a hundred years. Today refractometers are fairly common in many different fields. Examples for fields in which refractometers are used include food manufacturing industry, wood processing industry, chemical industry, and research projects in general.

The essential feature of refractometer measuring is analysis of an image produced by reflection of light. The purpose of this image analysis is to detect the position of the critical angle of total reflection, i.e. the boundary in which the light area changes to a dark area.

In previously known solutions, several different principles have been employed to determine the critical angle of total reflection. One of these principles is based on the idea that the brightness of the light area remains constant irrespective of the critical angle. Thereby the amount of light obtained from the entire image area corresponds with the proportion of light area in the total area. Many commercially available instruments employ the above-mentioned principle. However, a drawback of the principle is its sensitivity to variation in the light source, photocell and optical path.

Another known principle is a solution in which the image reflected from the optical window of the refractometer is observed by a line camera. A line camera has a plurality of light detectors, e.g. 256, integrated in a line into one and the same microcircuit. The camera displays the amounts of light measured by the detectors, one at a time. The position of the critical angle of total reflection can be determined by counting the detectors exceeding the threshold value. This kind of principle is employed e.g. in the PR-01-B, PR-01-E and PR-01-S refractometers manufactured and sold by K-Patents Oy.

The above principle operates rather well, but a drawback is that a line camera has a limited resolution capacity. The detecting element has to be large in regard to the wavelength of light, but the total length of the camera cannot in practice be increased infinitely. Another drawback is that in certain situations a single erroneous measuring point may notably distort the final result.

SUMMARY OF THE INVENTION

The object of the invention is to provide a method by which the drawbacks of the previously known techniques can be eliminated. This is achieved with the method according to the invention, which is characterized in that to the measuring data obtained from the light detectors is applied a mathematical model corresponding with the information provided by the measuring data and that the position of the boundary between the light and dark area is defined by means of this model.

The primary advantage of the method according to the invention is that the method defines resolution of fractions of a camera element, whereby the final result is more accurate than before. For example, the problems arising from lens resolution can thus be eliminated. The method according to the invention employs all the light detectors of the camera, whereby a single erroneous measuring point does not cause a notable error. The method according to the invention is also more stable than the previously known solutions. The earlier solutions have been restricted by the physical laws and prior art, but the present invention makes it possible to proceed further, i.e. to achieve accuracy that is better than what e.g. the physical characteristics of the apparatus would suggest.

BRIEF DESCRIPTION OF THE DRAWINGS

In the following the invention will be described in greater detail by means of an advantageous embodiment illustrated in the drawing, wherein.

DESCRIPTION

Figure 1:
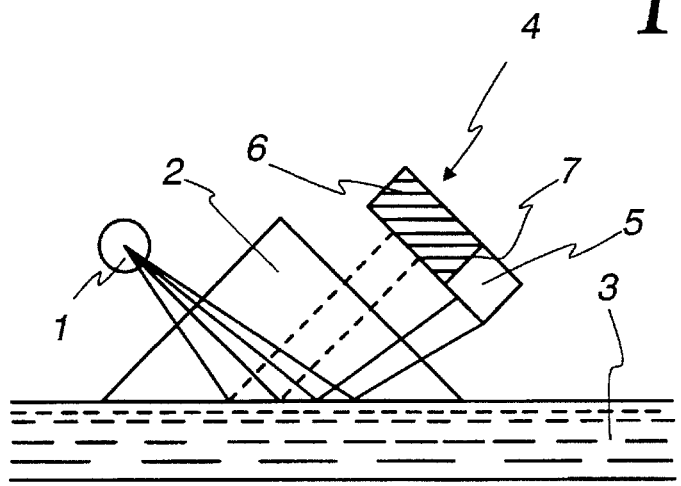
FIG. 1 shows a schematic view of the operating principle of a refractometer.

A refractometer used in a process, such as a wood processing process, for measuring the concentration of process liquid is called a process refractometer. A process refractometer is arranged in the process in such a way that the optical window at the measuring end of the refractometer, formed e.g. of a prism, is in contact with the process liquid. The process refractometer measures the refractive index of the process liquid by the total reflection taking place at the interface between the process liquid and the prism of the measuring end. FIG. 1 shows a schematic view of this measuring principle.

A beam of rays emitted from a light source 1 is transmitted to the interface between a prism 2 and a process liquid 3. Part of the beam of rays is totally reflected back from the liquid, whereas part is partly absorbed into the liquid. The reflection of the beam of rays produces an image 4, in which the position of a boundary 7 between a light area 5 and a dark area 6 depends on the critical angle of total reflection and thus on the refractive index. Determining of the position of the boundary 7 between the light area 5 and the dark area 6 in the image 4 defines the concentration of the process liquid. The position of the boundary 7 can be determined by means of light detectors arranged in a line. The number of light detectors used in the measuring is high; e.g. the PR-01-S process refractometer manufactured and sold by K-Patent Oy comprises 256 light detectors integrated into one and the same micro circuit. The detecting means comprising the light detectors transforms the image 4 into an electric signal dot by dot. The light detectors in the light area supply a certain kind of signal, and the light detectors in the dark area supply another kind of signal.

The above-described measuring principle is fully known to a person skilled in the art, and so it is not described in greater detail herein.

In previously known apparatuses the position of the boundary 7 between the light area 5 and the dark area 6 is directly determined by signals supplied by the light detectors. In practice the measuring is carried out such that the signals of the photocells are divided into high and low signals on the basis of a predetermined threshold value T, and the high signals are then counted. The number of high signals determines the breadth of the light area and thereby the position of the boundary 7, which is then converted into concentration units and indicated on an appropriate display or the like.

However, a drawback of the above-described determining method is that the internal inaccuracy of the refractometer distorts the final result. Examples for causes of inaccuracy include lens resolution and the fact that a single erroneous measuring point may at the worst distort the final result. In general, it is possible say that the accuracy is restricted by the physical laws and prior art.

Figure 2:
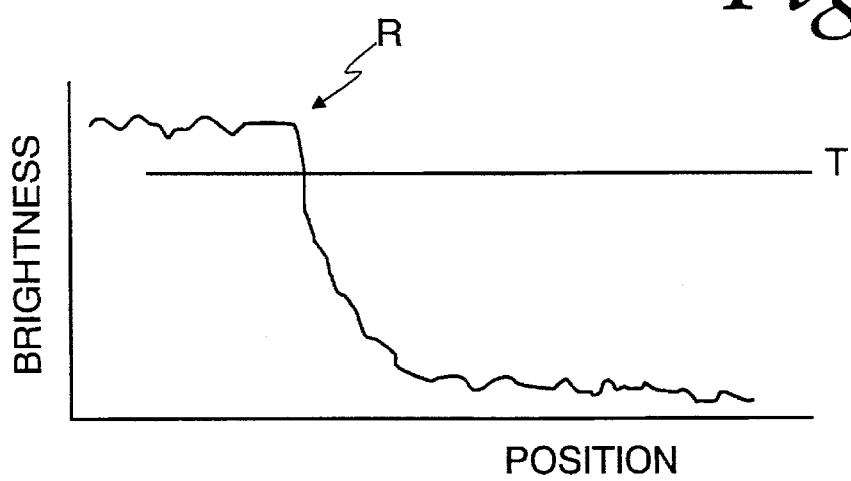
FIG. 2 shows a schematic view of brightness distribution of the image produced in the refractometer as a function of place.

FIG. 2 shows brightness distribution of the image 4 as a function of place, i.e. the brightness of the image 4 varies from the light area 5 to the dark area 6 in the manner illustrated in FIG. 2. The graph of FIG. 2 is based on the measuring points determined by the light detecting means. The significant point in FIG. 2 is point R, which stands for the critical angle of total reflection, i.e. boundary 7.

The invention provides a method by which the drawbacks of the prior art can be eliminated. The essential idea of the invention is that the position of the boundary 7 is not directly determined by the measuring data obtained from the light detecting means but that a mathematical model is reconstructed on the basis of the measuring data and the position of the critical angle of total reflection, i.e. the position of the boundary 7, is calculated by applying the model to the above-mentioned measuring data. The method according to the invention is thus characterized in that a mathematical model corresponding with the information provided by the measuring data is applied to the measuring data obtained from the light detectors and that the position of the boundary between the light area 5 and the dark area 6 is determined by the model. Advantageously, the model is applied to the brightness distribution of the image 4.

The resolution of the result calculated by the method according to the invention is better than what the size of the detecting element would suggest. It is to be noted that the detecting element must be large in regard to the wavelength of light but that the total length of the line camera, i.e. detector, cannot be increased infinitely, as stated above. The method according to the invention defines resolution of fractions of the detecting element. It is also to be noted that since the application of the model employs all the measuring points of the detecting means, a single erroneous measuring point does not cause notable errors.

Figure 3:
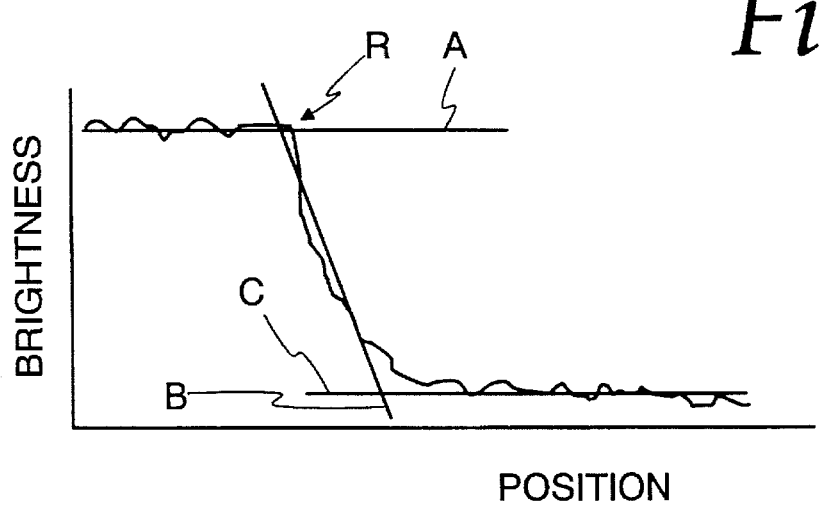
FIG. 3 shows a schematic view of a mathematical model applied to the measuring information of FIG. 2.

FIG. 3 shows by way of example how the method according to the invention can be applied. FIG. 3 shows a corresponding brightness distribution of the image 4 as FIG. 2. The graph concerned is thus based on the signals obtained from the light detectors. In the example of FIG. 3, three straight lines A, B and C are applied to the distribution defined by the light detectors. Line A represents the light area, line C the dark area and line B the transition area between the light and dark area. The position of the critical angle of total reflection, i.e. the position of the boundary 7, is found at the point where lines A and B intersect. The example is only intended to clarify the basic idea of the invention.

The above embodiment is not to be understood as restricting the invention in any way. The invention can be modified quite freely within the scope of the claims. It is thus clear that the invention is not restricted to a specified mathematical model, e.g. to the straight lines of FIG. 3, but that the invention can be applied in many different ways by employing different mathematical principles. A mathematical model can be applied to the brightness distribution of the image with the aid of the smallest sum of quadrates, and the measuring results can then be calculated from this model. The brightness distribution model contains in practice transcendent functions. Application of a model of this kind is usually iterative and therefore slow. The model can be simplified to be e.g. a polynomial function.

We claim:

1. A method for measuring a critical angle of total reflection of a liquid using a refractometer, said method comprising the steps of:

transmitting a beam of rays from a light source to an interface between said liquid and an optical window of said refractometer, whereby part of said beam is reflected back from said liquid and part of said beam is absorbed into said liquid, said reflected back part of said beam projecting an image onto a plurality of linearly arranged light detectors, each of said light detectors producing an output related to intensity of a portion of said image projected onto said light detector, said image having a light area and a dark area and a transition area therebetween;

constructing a mathematical model representing said image based on said outputs of said light detectors taken while the window of said refractometer is in contact with said liquid said mathematical model comprising a mathematical representation of said light area and a mathematical representation of said transition area; and determining said critical angle of total reflection based upon the relationship of said representations of said light area and transition area of said mathematical model constructed for said liquid.

2. A method in accordance with claim 1 wherein said mathematical model constructing step comprises constructing a straight line representation for said light area and a straight line representation for said transition area.

3. A method in accordance with claim 2 wherein said determining step comprises identifying the intersection of said straight line representation of said light area and said straight line representation of said transition area.

4. A method for determining a concentration of a liquid by determining a critical angle of total reflection of said liquid using a refractometer, said method comprising the steps of:

transmitting a beam of rays from a light source to an interface between said liquid and an optical window of said refractometer, whereby part of said beam is reflected back from said liquid and part of said beam is absorbed into said liquid, said reflected back part of said beam projecting an image onto a plurality of linearly arranged light detectors, each of said light detectors producing an output related to an intensity of a portion of said image projected onto said light detector, said image having a light area and a dark area and a transition area therebetween;

constructing a mathematical model representing said image based on said outputs of said light detectors taken while the window of said refractometer is in contact with said liquid, said mathematical model comprising a mathematical representation of said light area and a mathematical representation of said transition area;

determining said critical angle of total reflection based upon the relationship of said representations of said light area and said transition area of said mathematical model constructed to represent the image for said liquid; and calculating said concentration from said determination of said critical angle of total reflection, said critical angle of total reflection being a function of said concentration.

5. A method in accordance with claim 1 wherein said determining step comprises identifying an intersection of the mathematical representation of said light area and the mathematical representation of said transition area.

* * * * *

UNITED STATES PATENT AND TRADEMARK OFFICE
CERTIFICATE OF CORRECTION

PATENT NO. : 5,617,201
DATED : April 1, 1997
INVENTOR(S) : Jan KAHRE

It is certified that error appears in the above-indentified patent and that said Letters Patent is hereby corrected as shown below:

At column 4, line 37 (claim 1) after "and" insert --said--.

At column 4, line 44 (claim 3) change "the" to --an--.

Signed and Sealed this

Twenty-third Day of September, 1997

Attest:

BRUCE LEHMAN

Attesting Officer

Commissioner of Patents and Trademarks